United States Patent
Nakamura et al.

(10) Patent No.: US 6,390,669 B1
(45) Date of Patent: May 21, 2002

(54) HEAT FLUX TYPE DIFFERENTIAL SCANNING CALORIMETER

(75) Inventors: Nobutaka Nakamura; Ryoichi Kinoshita, both of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/351,504

(22) Filed: Jul. 12, 1999

(30) Foreign Application Priority Data

Jul. 14, 1998 (JP) ............................................ 10-198934

(51) Int. Cl.$^7$ ......................... G01N 25/00; G01K 17/00
(52) U.S. Cl. ........................... 374/12; 374/10; 374/31
(58) Field of Search ......................... 374/10, 12, 31, 374/11, 13, 33

(56) References Cited

U.S. PATENT DOCUMENTS

| | | | | |
|---|---|---|---|---|
| 3,995,485 A | * | 12/1976 | Beyer et al. | 374/33 |
| 4,095,453 A | * | 6/1978 | Woo | 374/13 |
| 4,149,401 A | * | 4/1979 | Hentze | 374/10 |
| 4,333,332 A | * | 6/1982 | Privalov | 374/10 |
| 4,368,991 A | * | 1/1983 | Hentze | 374/12 |
| 5,098,196 A | * | 3/1992 | O'Neill | 374/11 |
| 5,211,477 A | * | 5/1993 | Li | 374/33 |
| 5,248,199 A | * | 9/1993 | Reading | 374/11 |
| 5,295,745 A | * | 3/1994 | Cassettari et al. | 374/33 |
| 5,439,291 A | * | 8/1995 | Reading | 374/11 |
| 5,599,104 A | * | 2/1997 | Nakamura et al. | 374/12 |
| 5,711,604 A | * | 1/1998 | Nakamural | 374/12 |
| 5,842,788 A | * | 12/1998 | Danley et al. | 374/12 |
| 6,079,873 A | * | 6/2000 | Cavicchi et al. | 374/10 |

FOREIGN PATENT DOCUMENTS

| | | | | |
|---|---|---|---|---|
| EP | 645619 A2 | | 3/1995 | |
| FR | 2428837 | | 1/1980 | |
| JP | 356082436 A | * | 7/1981 | 374/10 |
| JP | 60-64250 | | 5/1985 | |
| JP | 0209158 | * | 10/1985 | 374/31 |
| JP | 360207046 A | * | 10/1985 | 374/31 |
| JP | 62231148 | | 10/1987 | |
| JP | 4348265 | | 12/1992 | |
| JP | 5223764 | | 8/1993 | |
| JP | 8247977 | | 9/1996 | |
| JP | 0255649 | * | 10/1998 | 374/31 |

\* cited by examiner

*Primary Examiner*—Diego Gutierrez
*Assistant Examiner*—Madeline Gonzalez
(74) *Attorney, Agent, or Firm*—Adams & Wilks

(57) ABSTRACT

A heat flux type differential scanning calorimeter has a heat reservoir made of a thermal conducting material. A thermally conductive plate is disposed in the heat reservoir for supporting an unknown sample and a reference sample symmetrically with respect to a center of the reservoir. A thermally conductive support member is disposed in contact with the thermally conductive plate and supports the thermally conductive plate in the heat reservoir. A heat buffer plate is disposed between the thermally conductive support member and the heat reservoir so that the thermally conductive support member and the heat reservoir are contacted only through the heat buffer plate.

14 Claims, 2 Drawing Sheets

HEAT FLUX TYPE DIFFERENTIAL SCANNING CALORIMETER

BACKGROUND OF THE INVENTION

The present invention relates to a heat analyzing apparatus for measuring how a material property changes with temperature. More specifically, the invention relates to a differential scanning calorimeter of a heat flux type for measuring a differential heat flow excessively dissipated from and absorbed by a sample as compared to a reference substance based on a temperature difference (differential heat) between the sample and the reference substance.

The conventionally used heat flux type differential scanning calorimeter has a detector structure of the type shown in FIG. 2 and FIG. 3.

The type of FIG. 2 has a detector in a flat plate form soldered to side surfaces of a heating oven formed of a thermally good conductor having a sectional H-character form. The heat flow path within the detector is in a two dimensional form directed radially inwardly from the heat oven side surfaces to a sample section and a reference section.

The type of FIG. 3 has a detector directly placed on a bottom plate of a heat oven formed of a thermally good conductor in a sectional H-character form, as seen in JP-A-60-64250U. The heat flow path within the detector is provided with a neck portion to suppress temperature distribution. The heat flows one-dimensionally to the sample section and the reference section.

In both the types of FIG. 2 and FIG. 3, the heat oven temperature is based on negative feedback control by a program temperature controller, and is accurately controlled linearly with respect to time according to a ramp function. At this time, since the temperature difference between the sample section and the reference section is proportional to a difference in flow of the heat absorbed by or dissipated from them, when multiplied by a proper coefficient, it is regarded as an output of a differential heat flow. In this manner, one type of the differential scanning calorimeter that has a temperature difference output multiplied by a proper coefficient into rating to be dealt with as an output of a differential heat flow is called a heat flux type differential scanning calorimeter.

In the differential scanning calorimeter of the FIG. 2 type, there is a tendency to cause in the heat oven side surfaces a temperature distribution in a direction of A of FIG. 2. In such a case, in the detector directly fixed to the heat oven side surfaces, a temperature difference appear between the sample section and the reference section even in a state that no sample is placed. Due to this, a differential heat flow signal is varied to result in a defect that the accuracy in measurement lowers.

Also, it is unavoidable for the detector to suffer exhaustion such as deterioration due to contamination caused by sample decomposition or exposure to high temperature. However, the detector is soldered to the heat oven side surfaces and difficult to be removed. There has been a necessity to replace the detector in accordance with its exhaustion together with a heat oven having its life still left.

On the other hand, the differential scanning calorimeter of the FIG. 3 type has been proposed in order to solve the above-described problem. However, because the heat flow path is one dimensionally, the efficiency of heat transfer is worse as compared to the two-dimensional structure in the FIG. 2 type. As a result, the time constant in heat flow detection increased, thereby lowering the detector response.

Furthermore, in both the FIG. 2 and FIG. 3 differential scanning calorimeter types, the heat oven of a good heat conductor in the sectional H-character form and the detector are directly soldered or contacted. As a result, it is difficult to avoid fine temperature vibration in the heat oven due to temperature control from vibrating the detector. Due to this, the differential scanning signal is readily ridden on by vibratory noise which results in a reduction or signal sensitivity.

SUMMARY OF THE INVENTION

In order to solve the above problem, the present invention is provided with a heating oven with a bottom plate having a cylindrical internal space, a heat buffer plate fixed on the bottom plate and formed of a material having a low heat conductivity, and a differential heat flow detector fixed on the heat buffer plate. The differential heat flow detector is fixed on the buffer plate by screw fastening, and can be mounted/dismounted and replaced if the screws are removed. Also, the differential heat flow detector is structured in a form that a heat conducting metal plate in a flat plate form is held by a heat conducting plate support member made of a thermally good conductor. A differential heat flow signal is outputted as a voltage between metal wires welded to the heat conducting plate. Further, the heat conducting metal plate is soldered at oval or elliptical formed peripheral end portion to the heat conducting plate support member. A pair of convex portions are formed in a longer axis direction. of the oval or elliptical of the heat conducting metal plate and in symmetrical position about a center thereof.

When the temperature of the heating oven is controlled according to a ramp function, one part of the heat flows through the heat buffer plate to the differential heat flow detector in a state that fine thermal vibration is filtered. In the differential heat flow detector, the heat conducting plate support member made of a thermally good conductor functions as a heat sink. Because a difference in heat which flows from the heat sink to a sample section and a reference section composing the pair of convex portions in the heat conducting metal plate is measured by a differential thermocouple formed between the heat conducting metal plate and the metal wire, thus functioning as a differential scanning calorimeter.

Figure 1:
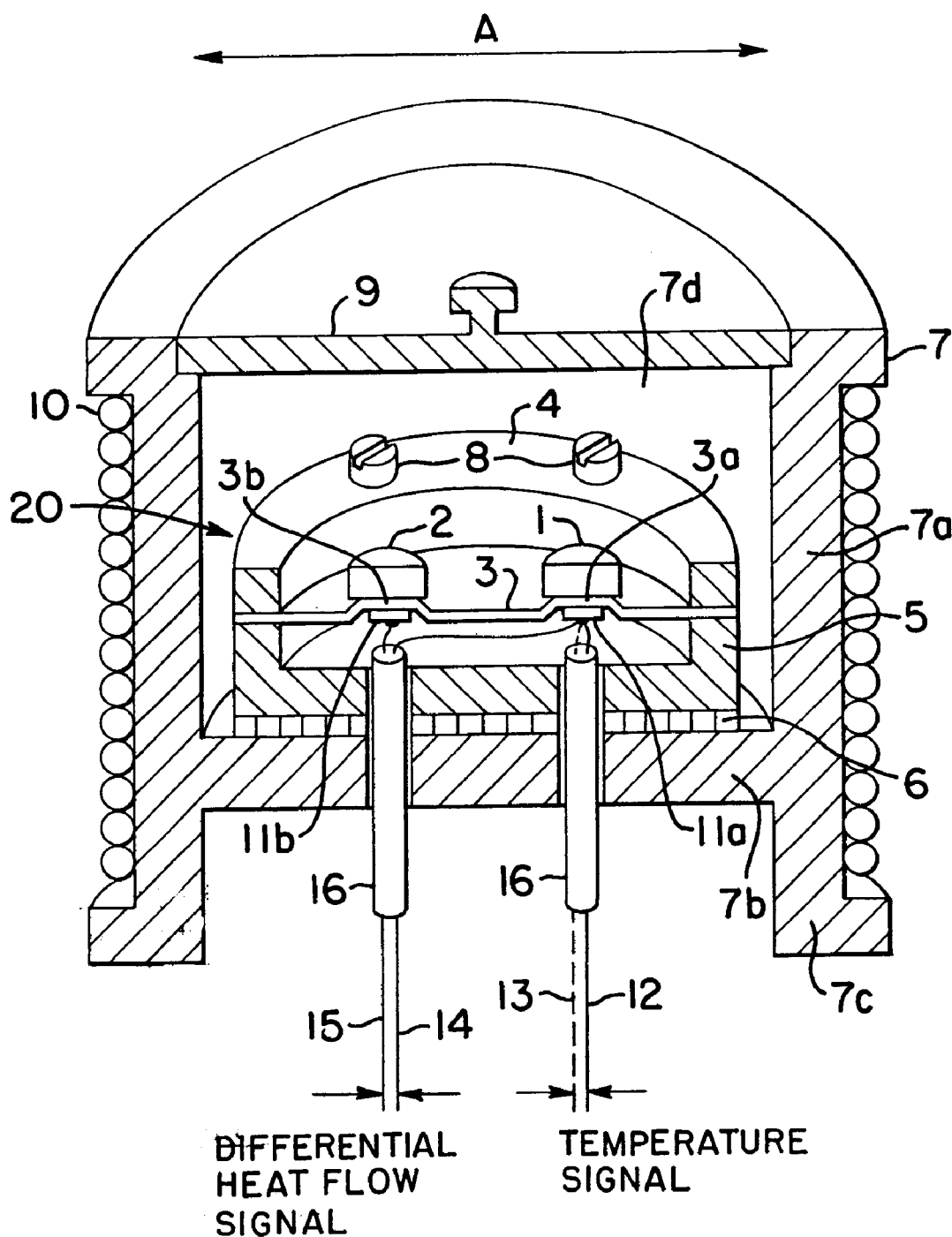
FIG. 1 is an explanatory view having a partly side sectional view showing one embodiment of the present invention.
Figure 2:
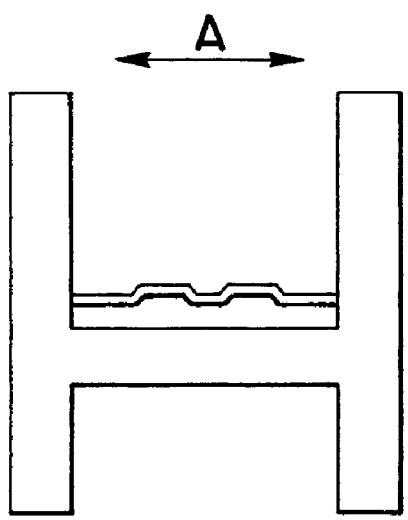
FIG. 2 is a side sectional view showing a conventional apparatus.
Figure 3:
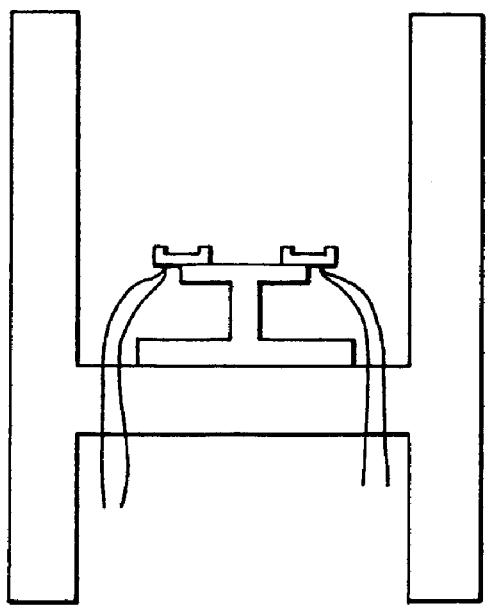
FIG. 3 is a side sectional view showing a conventional apparatus.

DESCRIPTION OF THE REFERENCE NUMERALS 1 sample vessel
2 reference vessel
3 heat conducting plate
3a sample section
3b reference section
4 upper support plate
5 lower support plate
6 heat buffer plate
7 heating oven 8 set screw
9 lid
10 heater
11a sample side chromel plate
11b reference side chromel plate
12, 14, 15 chromel wires
13 alumel wire
16 double cored insulation tube

DETAILED DESCRIPTION OF THE PREFERRED EMBODIMENT

Hereinafter, an example of a differential scanning calorimeter according to the present invention will be explained together with the drawing.

FIG. 1 shows a preferred embodiment of a differential scanning calorimeter according to the present invention, wherein reference character 1 is an unknown sample filled vessel and 2 is a reference substance filled vessel. The sample vessel 1 and the reference vessel 2 are respectively placed on convex portions symmetrically provided in a heat conduction plate 3 made of a constantan, i.e., a sample section 3a and a reference section 3b, and supported by a support member comprised of an upper support plate 4 and a lower support plate 5. The heat conduction plate 3 is a soldered through a silver solder in a form clamped in a sandwich form between the upper support plate 4 made of silver in a ring form and the lower support plate 5 made of silver in a cup form. The upper support plate 4 and the lower support plate 5 both have their circular outer peripheries and inner peripheries ovally hollowed out. The lower support plate 5 has, at an underside, an inconel-made heat buffer plate 6 which has high heat proof quality and low heat conductivity as compared to silver. Incidentally, the lower support plate 5 and the heat buffer plate 6 have at nearly centered two positions signal line withdrawing small holes in two positions and fixing screw through-holes in outer four positions.

Reference character 7 is a cylindrical heat reservoir or oven made of silver in a sectional H-character form, and the heat oven 7 is wound at a side surface by a heater 10 with an insulation coating. The heat oven 7 has a side wall portion 7a, a base portion 7b, and a support portion 7c. The upper support plate 4, the heat conduction plate 3, the lower support plate 5 and the heat buffer plate 6 are fixed to the heat oven 7 through set screws 8 at 4 positions (two positions only illustrated). A silver lid 9 is placed on an upper portion of the heat oven 7 to form a closed, cylindrical internal space 7d including the sample section 3a and the reference section 3b, thus achieving thermal evenness by eliminating temperature fluctuation due to convection.

Also, the upper support plate 4, the heat conduction plate 3 and the lower support plate 5 have a side surface outer diameter smaller than an inner diameter of the heat oven 7, resulting in free of contact. Accordingly, even where there is a temperature distribution in a direction A of an inner diameter of the heat oven 7, the temperature distribution does not be conveyed to the heat conduction plate 3. The most part of the heat flow directed from the heat oven 7 to the heat conduction plate 3 is conducted to the heat conduction plate 3 by way of the bottom plate of the heating oven 7 and the lower support plate 5. Accordingly, the temperature distribution in a planar direction within the heat conduction plate 3 is greatly reduced as compared to a method that heat directly comes from the side surfaces of the heat oven 7.

On an underside of the sample portion 3a and the reference portion 3b of the heat conduction plate 3, small-sized chromel-made disks 11a and 11b are respectively spot-welded at multiplicity of points. Further, in a bottom surface center of the sample-side chromel plate 11a, chromel wires 12, 14 and an alumel wire 13 are welded. On the other hand, at a bottom surface center of the reference-side chromel plate 11b, a chromel wire 15 is welded.

The cromel wire 12 and the alumel wire 13 are passed to the underneath of the sample section 3a by way of a sample-side alumina-made double-cored insulation tube 16 penetrated through the lower support plate 5, the heat buffer plate 6 and the heat oven 7. Also, the chromel wire 14 and 15 are passed to the underneath of the reference section 3b by way of a reference-side alumina-made double-cored insulation tube 16.

By the foregoing construction, a differential heat flow detector 20 of the heat flux type differential scanning calorimeter comprises the heat conduction plate 3, the support member 4, 5, the disks 11a, 11b, the wires 12–15 and the insulation tube 16.

Next, the operation of the apparatus shown in FIG. 1 is explained.

First, a measurer opens the lid 9, places on the sample section 3a and the reference section 3b, respectively, a sample vessel 1 packed with a sample to be measured and a reference vessel 2 packed with a reference substance having been confirmed of thermal stability in the temperature range that measurement is to be made, and then closes the lid 9.

Next, the measurer inputs a temperature program to a heating oven temperature controller (not shown), to give an instruction of starting measurement. The temperature controller supplies a power to the heater 10 such that an actually measured temperature at a particular point of the heating oven 7 is brought into agreement with the programmed temperature by a well-known negative feedback control, thus exactly controlling the temperature of the heating oven 7.

If a temperature difference is caused between respective parts such as the heating oven 7, the heat buffer plate 6, the lower support plate 5 and the heat conduction plate 3, then a heat flow occurs in proportion to the temperature difference and thermal conductance. As a result, the temperature of the sample vessel 1 and reference vessel 2 varies following a temperature of the heat oven 7. At this time, the temperature of the sample within the sample vessel 1 is accurately measured by a chromel-alumel thermocouple with the chromel wire 12 and alumel wire 13 soldered to the underside of the sample-side chromel plate 11a. On the other hand, a temperature difference between the sample vessel 1 and the reference vessel 2, which is an origin of a differential heat flow signal between the sample and the reference substance is determined, as follows.

In a circuit from the chromel wire 14 via the sample-side chromel plate 11a, sample section 3a, heat conduction plate 3, reference section 3b and reference-side chromel plate 11b to the chromel wire 15, the chromel wire 14 and the sample-side chromel plate 11a as well as the reference-side chromel plate 11b and the chromel wire 15 are formed of a same material chromel. Accordingly, if the temperature of each section changes, no electromotive force is generated. Also, because the interior of the heat conduction plate 3 is formed of a same material constantan, a temperature change of each section if caused generates no electromotive force. On the other hand, chromel-constantan multiple points of junction points are formed between the sample-side chromel plate 11a and the sample section 3a. The potential of chromel side 11a, 14 increases with increase in average temperature on the junction points. Similarly, in the junction point of the reference-side chromel plate 11b and the reference section 3b, the potential on the chromel side 11b, 15 increases with increase in average temperature on the junction point portion. In this manner, it is understood that the potential difference between the chromel wires 14 and 15 represents an electromotive force of a differential thermocouple representing a difference between a junction average temperature between the sample section 3a and the sample-side chromel plate 11a and a junction average temperature between the sample section 3b and the sample-side chromel plate 11b. Accordingly, it can be seen that the potential difference between the chromel wires 14 and 15 represents a temperature difference between the sample vessel 1 and the reference vessel 2 as measured by a chromel-constantan thermocouple.

In order to calibrate the heat flow sensitivity of the present apparatus, the temperature difference may be divided by a thermal resistance of heat flow detection according to the principle of heat flux type differential scanning calorimeter. Also, the output can be calibrated by experimentally determining the heat resistance by measuring enthalpy-known latent heat such as melting heat quantity of indium so that the peak area of a differential heat flow signal areas with the known latent heat.

As above, according to the present invention, because there in no contact between the heat oven side surface and the differential heat flow detector side surface, even if a temperature distribution which is liable to occur in the heat oven side surface occurs, a temperature difference hardly appears between the sample section 3a and the reference section 3b thus providing an effect of readily stabilizing the differential heat flow signal.

Also, the detector formed by the upper support plate 4, the heat conduction plate 3 and the lower support plate 5 is merely fastened by set screws 8 to the heat oven 7 through the heat buffer plate 6. Because no seizure occurs between the silver and inconel at a temperature of less than 750 degrees, an effect was also obtained that, if the wires 12–15 are removed, only the detector can be replaced as a single unit.

Further, because the heat flow buffer plate is interposed between the heat oven and the detector, it is possible to prevent fine temperature vibration caused by heat oven temperature negative feedback from being conveyed to the detector. Thus, an effect was obtained that signal accuracy is improved.

Moreover, because the heat flow path within the detector is two dimensionally configured, the time constant for heat flow detection can be shortened with a result that a differential scanning calorimeter having an acute peak and high in response was provided. In particular, in the present invention the use of a structure of soldering the heat conduction plate peripheral end in an oval form as a compact shape including the sample section and the reference section in symmetrical positions can reduce the thermal capacity and heat resistance within the heat conduction plate and greatly improve the response, as compared to the conventional example having a circular peripheral end.

What is claimed is:

1. A heat flux type differential scanning calorimeter comprising: a heating oven made of a thermal conducting material and having a bottom portion and a wall portion forming a cylindrical internal space; a heat buffer plate disposed on the bottom portion of the heating oven and formed of a material having a heat conductivity lower than that of the thermal conducting material of the heat oven; and a differential heat flow detector removably mounted on the heat buffer plate so that the differential heat flow detector is not directly contacted with the heating oven and the heating oven and the differential heat flow detector are contacted only through the heat buffer plate; wherein the differential heat flow detector comprises a heat conducting metal plate for supporting an unknown sample and a reference sample within the internal space of the heating oven, a heat conduction support member for supporting the beat conducting metal plate and formed of a material having a heat conductivity higher than that of the heat buffer plate, and a differential thermocouple having a plurality of metal wires connected to the heat conducting metal plate for measuring a heat flow in the heat conducting metal plate in accordance with a difference in heat flow absorbed or dissipated by the unknown sample and the reference sample by application of a voltage between the metal wires.

2. A heat flux type differential scanning calorimeter as recited in claim 1; wherein the heat conducting metal plate has a peripheral end portion connected to the heat conduction support member, and a pair of convex portions each for supporting a respective one of the unknown sample and the reference sample symmetrically with respect to a center of the heat conducting plate.

3. A heat flux type differential scanning calorimeter as recited in claim 2; wherein the peripheral end portion of the heat conducting metal plate is generally oval-shaped.

4. A heat flux type differential scanning calorimeter as recited in claim 2; wherein the peripheral end portion of the heat conducting metal plate is generally elliptical-shaped.

5. A heat flux type differential scanning calorimeter as recited in claim 1; wherein each of the heat conduction support member, the heat buffer plate and the bottom portion of the heating oven has a plurality of through-holes through which the metal wires pass.

6. A heat flux type differential scanning calorimeter comprising: a heat reservoir made of a thermal conducting material and having a center; a thermally conductive plate disposed in the heat reservoir for supporting an unknown sample and a reference sample symmetrically with respect to the center of the reservoir; a thermally conductive support member disposed in contact with the thermally conductive plate and supporting the thermally conductive plate in the heat reservoir; and a heat buffer plate disposed between the thermally conductive support member and the heat reservoir so that the thermally conductive support member and the heat reservoir are contacted only through the heat buffer plate.

7. A heat flux type differential scanning calorimeter according to claim 6; wherein the thermally conductive plate has a peripheral end portion and a pair of convex portions each for respectively supporting the unknown sample and a reference sample.

8. A heat flux type differential scanning calorimeter according to claim 7; wherein the peripheral end portion of the thermally conductive plate is generally oval-shaped.

9. A heat flux type differential scanning calorimeter according to claim 7; wherein the peripheral end portion of the thermally conductive plate is generally elliptical-shaped.

10. A heat flux type differential scanning calorimeter according to claim 6; wherein the thermally conductive support member comprises an upper support portion and a lower support portion disposed on the heat buffer plate; and wherein the thermally conductive plate is supported between the upper and lower support portions at the peripheral end portion of the thermally conductive plate.

11. A heat flux type differential scanning calorimeter according to claim 6; wherein the heat reservoir has a base portion supporting the heat buffer plate; and wherein the thermally conductive support member, the heat buffer plate and the base portion of the heat reservoir have a plurality of aligned through-holes.

12. A heat flux type differential scanning calorimeter according to claim 11; further comprising a differential thermocouple having a plurality of metal wires connected to the thermally conductive plate and extending through respective through-holes of the thermally conductive support member, the heat buffer plate and the base portion of the heat reservoir for measuring a heat flow in the thermally conductive plate in accordance with a difference in heat flow absorbed or dissipated by the unknown sample and the reference sample.

13. A heat flux type differential scanning calorimeter comprising: a heat reservoir made of a thermal conducting material and having a center; a heater for heating the heat reservoir; a thermally conductive plate disposed in the heat reservoir for supporting an unknown sample and a reference sample symmetrically with respect to the center of the reservoir; a thermally conductive support member disposed in contact with the thermally conductive plate and supporting the thermally conductive plate in the heat reservoir; and a heat buffer plate disposed between the thermally conductive support member and the heat reservoir for suppressing thermal vibrations generated by negative feedback from heat energy in the heat reservoir.

14. A heat flux type differential scanning calorimeter according to claim 13; wherein the thermally conductive support member and the heat reservoir are contacted only through the heat buffer plate.

* * * * *